United States Patent
Anderson et al.

(10) Patent No.: US 12,222,316 B2
(45) Date of Patent: Feb. 11, 2025

(54) SEMICONDUCTOR DEVICE PROVIDING A BIOSENSOR TO TEST FOR PATHOGEN

(71) Applicant: IceMos Technology Limited, Belfast (GB)

(72) Inventors: Samuel J. Anderson, Tempe, AZ (US); Hugh J. Griffin, Belfast (GB)

(73) Assignee: IceMos Technology Limited (GB)

( * ) Notice: Subject to any disclaimer, the term of this patent is extended or adjusted under 35 U.S.C. 154(b) by 1017 days.

(21) Appl. No.: 17/171,691

(22) Filed: Feb. 9, 2021

(65) Prior Publication Data

US 2022/0236214 A1 Jul. 28, 2022

Related U.S. Application Data

(63) Continuation-in-part of application No. 17/158,609, filed on Jan. 26, 2021, now abandoned.

(51) Int. Cl.
*G01N 27/414* (2006.01)
*G01N 27/327* (2006.01)
*G01N 33/539* (2006.01)

(52) U.S. Cl.
CPC ..... *G01N 27/4145* (2013.01); *G01N 27/3272* (2013.01); *G01N 27/4146* (2013.01); *G01N 33/539* (2013.01)

(58) Field of Classification Search
None
See application file for complete search history.

(56) References Cited

U.S. PATENT DOCUMENTS

2006/0075818 A1* 4/2006 Huang ................. B06B 1/0292
73/649
2008/0121611 A1* 5/2008 Miller ................. B81C 1/00158
216/13

(Continued)

FOREIGN PATENT DOCUMENTS

CN 106646175 A * 5/2017 ......... G01R 31/2648
WO 2007139511 A1 6/2007
WO 2009088408 A1 7/2009

OTHER PUBLICATIONS

English translation of CN-106646175-A. (Year: 2017).*

(Continued)

*Primary Examiner* — Lore R Jarrett
(74) *Attorney, Agent, or Firm* — Robert D. Atkins; PATENT LAW GROUP: Atkins and Associates, P.C.

(57) ABSTRACT

An atomic level deposition for mass functionalization of a cavity filled with a pathogen sensitive antibody reagent to functionalize each biosensor using atomic level vapor phase deposition enables high volume production of this sensor technology. A biosensor has a first substrate and a second substrate with a cavity formed in the first substrate to form a membrane. Holes are formed through the second substrate. An aluminum oxide layer is formed over the cavity and into the holes to form cores. The cavity is filled with a pathogen sensitive antibody reagent. A biofluid sample with the pathogen is deposited over the membrane. The biofluid is drawn through the cores to mix with the antibody reagent. The antibodies combine with the pathogen to change the impedance along the current path. The presence of the pathogen changes the ionic current flow through the biosensor for a positive detection of the pathogen.

28 Claims, 12 Drawing Sheets

(56) References Cited

U.S. PATENT DOCUMENTS

| | | | |
|---|---|---|---|
| 2012/0037591 A1 | 2/2012 | Tringe et al. | |
| 2013/0168781 A1* | 7/2013 | Mantese | H01J 1/3044 |
| | | | 257/E29.166 |
| 2013/0306549 A1* | 11/2013 | Tringe | B01D 71/0213 |
| | | | 210/500.21 |
| 2018/0259480 A1 | 9/2018 | Karhanek et al. | |
| 2021/0233864 A1* | 7/2021 | Muthuseenu | H01L 23/552 |
| 2021/0239647 A1 | 8/2021 | Chang et al. | |
| 2021/0239688 A1* | 8/2021 | Chang | A61B 5/685 |

OTHER PUBLICATIONS

Senkei Umehara et al., "Label-Free Biosensing with Functionalized Nanopipette Probes", PNAS, vol. 106, No. 12, pp. 4611-4616, Mar. 24, 2009.

Ha, Jang-Hoon et al., "Preparation processes and characterizations of alumina-coated alumina support layers and alumina-coated natural material-based support layers for microfiltration." Ceramics International 42.12 (2016): 13796-13804. (Year: 2016).

* cited by examiner

SEMICONDUCTOR DEVICE PROVIDING A BIOSENSOR TO TEST FOR PATHOGEN

CLAIM TO DOMESTIC PRIORITY

The present application is a continuation-in-part of U.S. patent application Ser. No. 17/158,609, filed Jan. 26, 2021, which application is incorporated herein in its entirety by reference.

FIELD OF THE INVENTION

The present invention relates in general to a semiconductor device and, more particularly, to a semiconductor device and method providing a biosensor to test for a pathogen.

BACKGROUND OF THE INVENTION

In the field of public health, as performance analyses and medical diagnoses advance, sensors such as biosensors become essential. Biosensors are capable of detecting, proteins, such as antigens and antibodies and deoxyribonucleic acid (DNA), which are all deeply involved in the phenomena of life.

The flu has been around for more than 100 years and remains a deadly virus. While the flu today is managed through flu shots every winter, thousands of people die each year from the flu in the United States of America. SARS-COV-2 has proven to be more deadly than the flu by at least by an order of magnitude and as the SARS-COV-2 virus could persist for many years and, even if SARS-COV-2 is eradicated, other diseases are almost certain to occur in the future.

In recent history, global travel reaches a wide population with air travel bringing people together within a day or two across the globe. Yet, with all the benefits of global travel come some disadvantages. Perhaps the biggest disadvantage is that an outbreak of disease, such as the novel coronavirus or COVID 19, can spread around the world as fast as infected people can travel. The world population lives in a new era where pandemics are here and will likely alter the course of every aspect of life. As it is certain that people will continue air travel, technologists and scientists need to harness their skills and apply scientific principles to ideas that can engineer a way to aid countries, companies, and individuals on a path back to a quality of life approaching that of a pre-pandemic world.

To live in a pandemic world, a major concern will be test availability and test accuracy. The novel coronavirus itself is very small about one micrometer in diameter and now causes scientists to think of ways to defend humankind against a very tiny viral speck that has caused great economic and social damage to humankind. The polymerase-chain-reaction (PCR) swab test, involving a nasopharyngeal swab, is the standard, most reliable diagnostic method. Chemicals are used to amplify the virus's genetic material from the swab so that it can be analyzed. The test sample goes through a number of cycles in the lab before enough virus is recovered. Yet, swab-type coronavirus diagnostic tests can be inaccurate. A false positive result erroneously labels a person infected, with consequences including unnecessary quarantine and contact tracing. False negative results are more consequential, because infected persons who might be asymptomatic may not be isolated and can infect others. Nasal-swab type detection tests have been used to diagnose suspected cases at a clinic or hospital, where test results take anywhere from 15 minutes to 8 hours.

With the threat of the novel SARS-COV-2 coronavirus concerning health officials globally, there is urgent need for better methods of mass screening to contain the spread of the virus. Scanning foreheads of individuals for fever is widely used for screening, but temperature scanning cannot detect asymptomatic infections, nor can it distinguish the novel coronavirus from other respiratory illnesses. Swab-type coronavirus detection tests are slow and inefficient, making them impractical for mass screening, such as schools, workplaces, universities, and entertainment and sports venues.

DETAILED DESCRIPTION OF THE DRAWINGS

The present invention is described in one or more embodiments in the following description with reference to the figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

Figure 1:
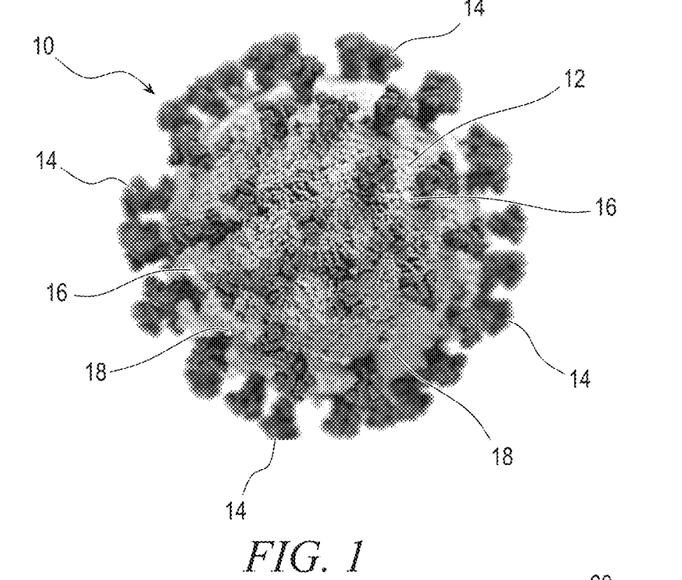
FIG. 1 illustrates a single SARS-COV-2 viral particle.

FIG. 1 is a single SARS-COV-2 viral particle 10 with E protein 12, spike (S) protein 14, and M protein 16 extending from envelope 18. Cells are the basic units of all living organisms that can independently exist. Any attack on the human cells in your body may become life threatening. The SARS-COV-2 is the virus that causes COVID-19 and can only be seen through a transmission electron microscope (TEM). Under a TEM image, SAR-COV-2 has a crown-like appearance, hence the name coronavirus comes from the Latin word "coronam" or "corona".

During the infection process, the SARS-COV-2 virus particle 10 attacks the host's cells by attaching to receptors ACE2 in the host cell. S proteins 14 bind the virus to the surface of the cellular wall. When conditions are right, SARS-COV-2 virus particle 10 infiltrates the living host cell. Once inside the cell, SAR-COV-2 virus 10 enlists the infected cell to produce RNA and proteins. The virus takes over the cell's reproductive systems and can copy coronavirus RNA in bulk. The RNA tells the cell how to make viral proteins. The viral proteins are used to build a new generation of coronaviruses within the cell. The new released viruses travel in special compartments to leave the cell and infect adjacent healthy cells, while remaining coronaviruses can replicate within the parent cell attacking the parent cell until eventually destroying the host cell. The replication continues through every cell entered causing eventual destruction of the human cell structure until the virus is rendered inactive by host antibodies, medical intervention, or death of the host.

Given the challenges of the SARS-COV-2 virus and the cost of responding to the virus in a pandemic world, there is a need for faster and more accurate diagnostic testing that can be cost effectively applied worldwide. A rapid acceleration of diagnostics test (RADx) has been proposed that could potentially test 100's of millions of people per day. In one embodiment, RADx is based on nanopipette principles and implemented using scalable silicon on insulator micro electromechanical system (SOI MEMS) semiconductor manufacturing technology. Nanopipettes can uniquely identify biomolecules, such as proteins, based on differences in size, shape, and electrical charge. These differences are determined by the detection of ionic current as proteins interact with the nanopipette tip coated with probe molecules. The antibody-antigen reaction in the sample solution causes a change in the surface charge as a result changing the conductivity of the solution. That change in conductivity measures the concentration of the target SARS-COV-2 and provides a measurement proportional to the viral load of the nanoparticles infecting the human cells.

Figure 2A:
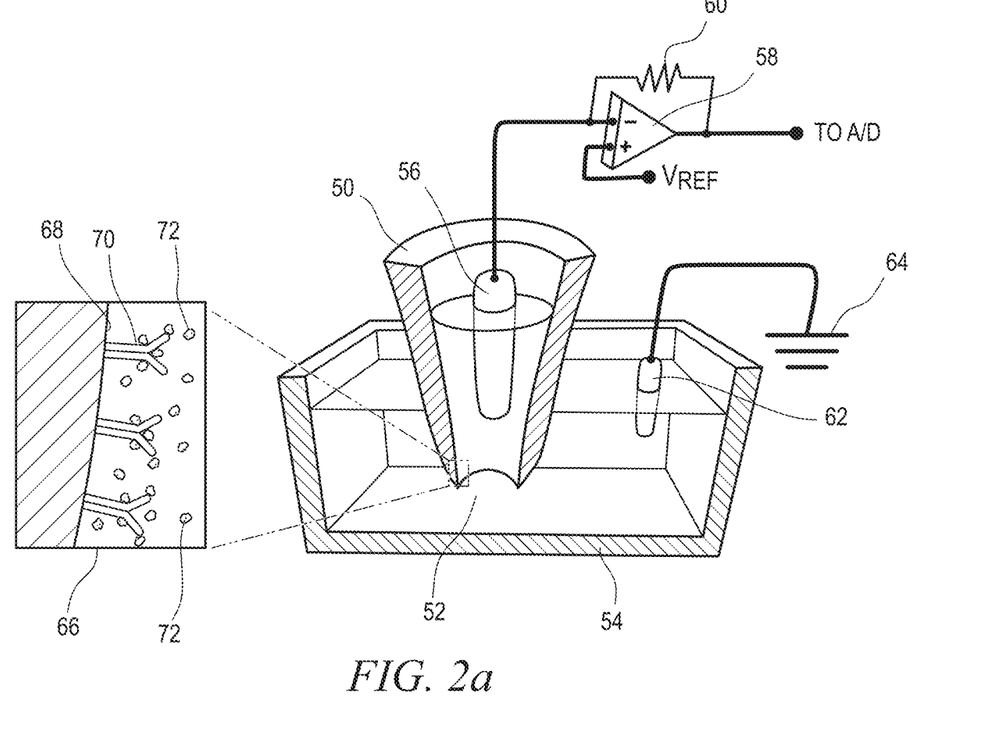
FIGS. 2a-2c illustrate testing for a pathogen using nanopipette.

FIG. 2a illustrates a simplified technique using nanopipettes and current spectroscopy to detect to the target SARS-COV-2 virus. Nanopipette 50 is partially immersed in electrolyte/analyte solution 52, e.g., potassium chlorine (KCl), contained within vessel 54. Nanopipette 50 includes electrode 56 also partially immersed in electrolyte/analyte solution 52. Electrode 56 is connected to the inverting input of low noise amplifier 58. The non-inverting input of amplifier 58 receives a reference voltage $V_{REF}$. Resistor 60 is connected between the output of amplifier 58 and its inverting input to set the gain of the amplifier. The output of amplifier 58 is routed through an analog-to-digital converter to a computer system (not shown) to analyze the measurements. Electrode 62 is partially immersed in electrolyte/analyte solution 52 and connected to ground terminal 64. Amplifier 58 measures the current at the tip of nanopipette 50, i.e., changes in current measures concentration of the target.

Nanopipette 50 has tip orifices on the order of tens to hundreds of nanometers (nm). Nanopipette 50 makes nanofabrication possible at liquid/solid interfaces. The technology is being applied to COVID-19 detection in an antibody/antigen reaction causing a change in the surface charge resulting in changes in the conductivity of the sample solution that can be directly related to COVID-19 detection.

To implement an SOI MEMS nanopipette, atomic level deposition (ALD) deposits alumina or aluminum oxide on inner wall 68 of nanopipette 50 and along the backside of the membrane acting as an electrode that is in intimate contact with solution 52 where the specific antibodies for SARS-COV-2 reaction solution reside. SARS-COV-2 has a positive charge and the antibody reagent solution has a negative charge. The antibodies are attracted to the alumina electrode on the backside of the membrane. Alumina also serves as a way to narrow the thickness of nanopipette 50 so that the sample nasal fluid, saliva, or other biofluids containing SARS-COV-2 is in contact with the reaction group (a binder reference buffer solution) that selectively reacts with the specific SARS-COV-2 particle on the alumina electrode causing a change in electrical current that can be measured accompanying the chemical reaction that takes place when the antibodies combine with the SARS-COV-2 particle. The alumina electrode directly detects the change in electrical current caused by a change in impedance due to the chemical reaction.

Figure 2B:
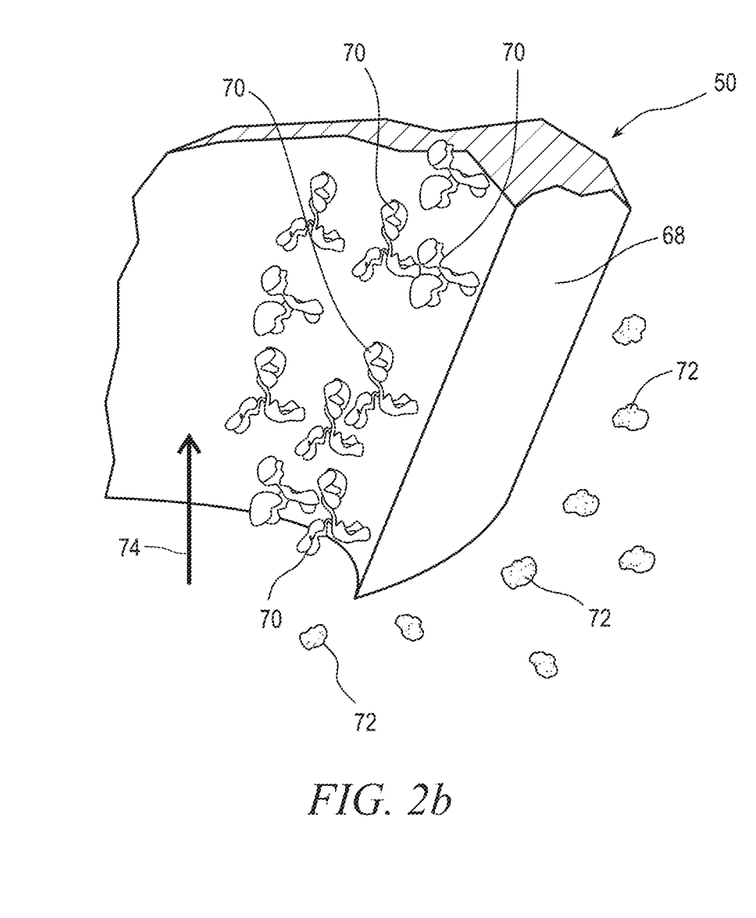
Figure 2C:
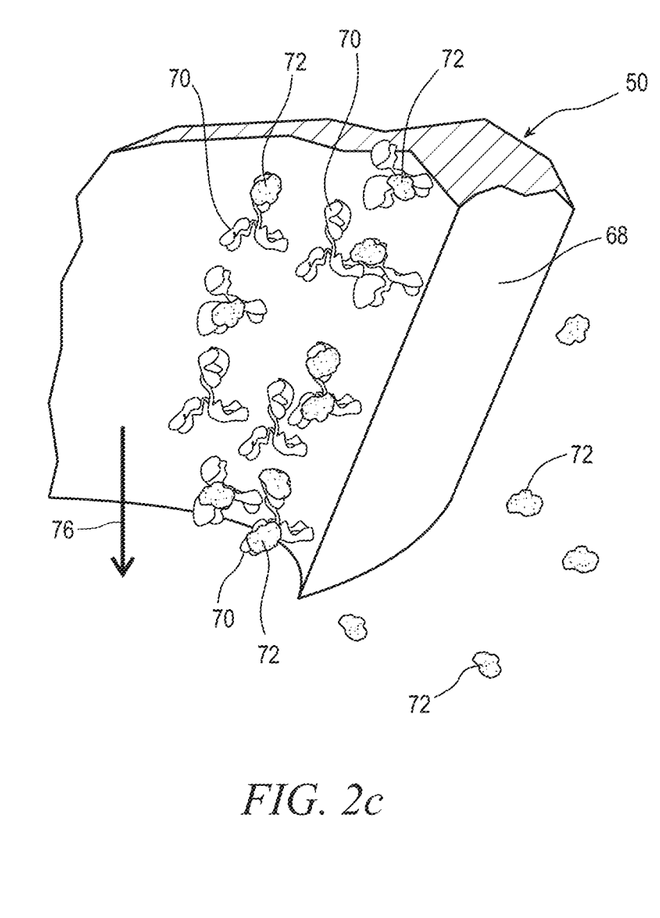

Window 66 illustrates an exploded view of inner wall 68 of nanopipette 50 with probes 70 extending from the inner wall. Nanopipette 50, including inner wall 68 and probes 70, is surrounded by a sample of nasal fluid, blood, saliva, or other biofluids, potentially containing particles of coronavirus 72. An electrical current flows through the probe tip causing particles of coronavirus 70 to emit an electronic charge. The charged particle 72 is attracted to probe 70 and causes a change in electrical current that is proportional to the amount of coronavirus in the sample. The current spectroscopy measures the change of charge on the nanopipette sensor tip caused by coronavirus particles. FIG. 2b illustrates SARS-COV-2 virus 72 attaching to probes 70 with the direction of current as arrow 74. FIG. 2c illustrates SARS-COV-2 virus 72 attaching to probes 70 with the direction of current as arrow 76.

Probes 70 immobilized by SARS-COV-2 virus can be implemented on SOI-MEMS-ALD manufacturable alumina nanopipette electrode tip. The nanopipette manufactured using deep reactive ion etching to create the nanocores and atomic level deposition precisely control the diameter of the nanocores and the thickness of the electrode on the backside of the membrane. The DRIE etch process leaves a scalloped side wall that can cause a problem for the flow of the nasal fluid, blood, saliva, or other biofluids through the nanopipette. To avoid this issue a sacrificial thermal oxide is grown on the inner wall of the nanopipette and then removed by wet chemistry following by hydrofluoric acid (HF) vapor phase fuming to smooth the inner wall. Then the atomic level deposition of a material such as alumina or any other material that enhances wetting of the nasal fluid, blood, saliva, or other biofluids through the nanopipette in addition to precisely controlling the diameter of the nanocores and thickness of the electrode on the backside of the membrane. The removal of these inner wall scallops is important to the surface chemistry that enables an electrical signal to be generated that is directly proportional to the viral load.

Figure 3A:
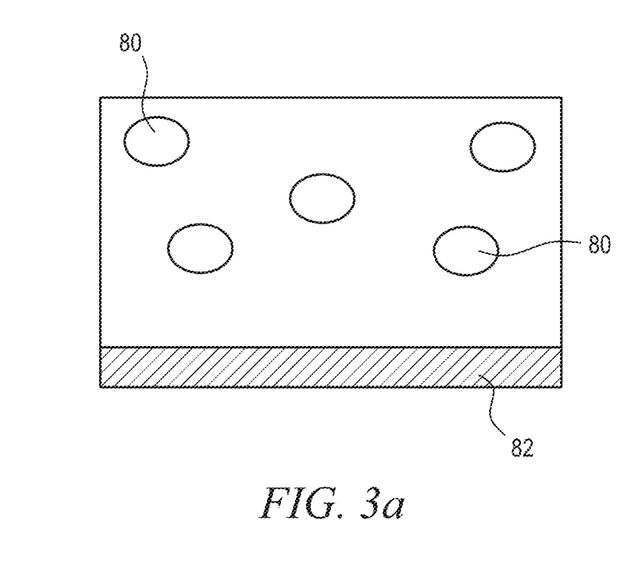
FIGS. 3a-3d illustrate plasma enhanced chemical vapor deposition.
Figure 3B:
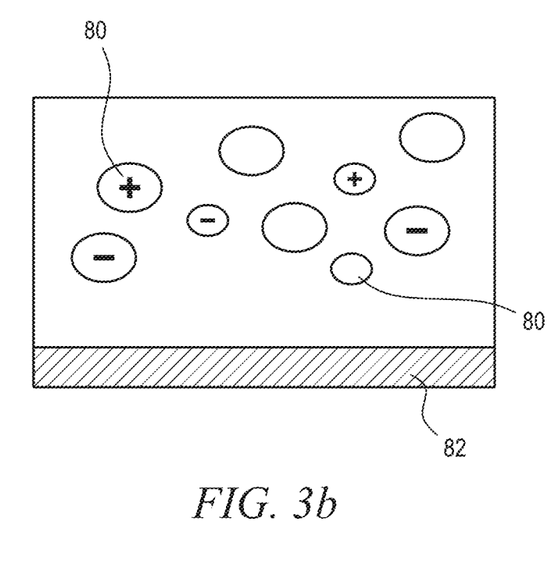
Figure 3C:
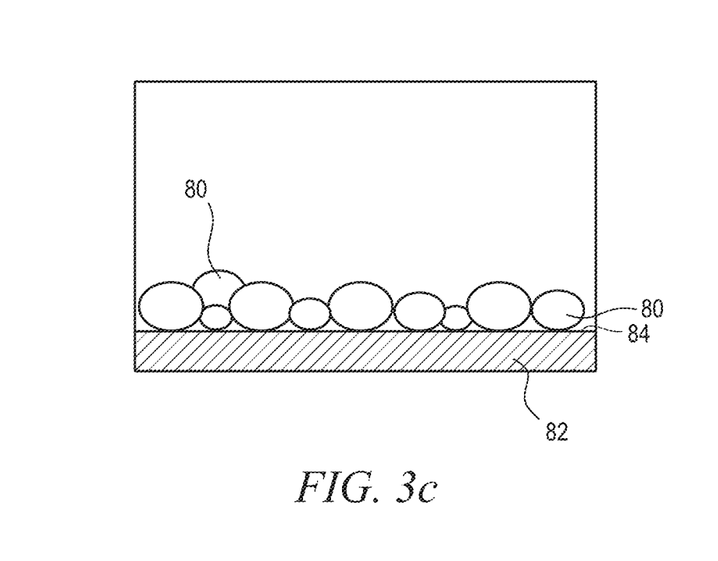
Figure 3D:
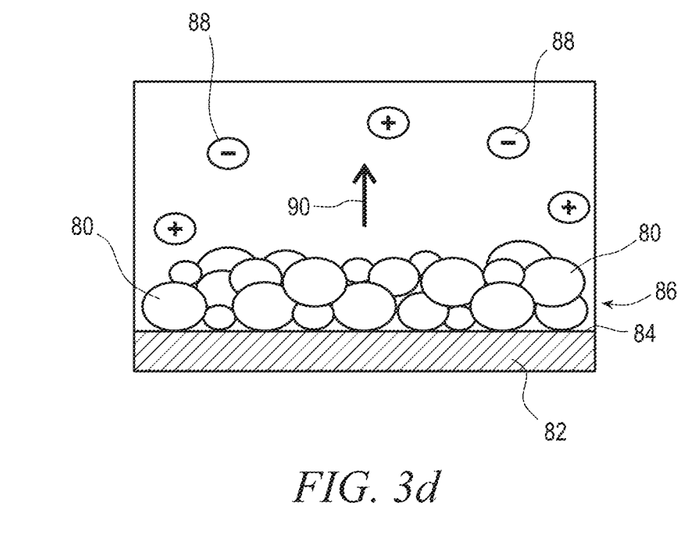

FIGS. 3a-3d illustrate plasma enhanced chemical vapor deposition (PECVD) ALD where a vapor phase is capable of producing thin films of a variety of materials. Based on sequential, self-limiting reactions, ALD offers exceptional conformality on high-aspect ratio structures, thickness control at the angstrom level, and tunable film composition. In FIG. 3a, precursors 80 flow into chamber 82. FIG. 3b shows plasma creating a mix of positive and negative species of precursors 80. FIG. 3c shows how species absorb on surface 84 of chamber 82 and react. FIG. 3d shows thin film 86 growing and byproducts 88 released in the direction of arrow 90.

In addition to using ALD to control the nanopipette thickness, ALD is later used to make the nanopipette functional in wafer form. Once the SOI-MEMS-ALD nanopipette has been fabricated in wafer form where up to tens of thousands of non-functional biosensor die are on the wafer it is then made functional by introduction of the reagent buffer solution in vapor phase into each nanopipette nanocore and cavity using atomic level vapor phase deposition using the same principle described in Alumina deposition of FIGS. 3a-3d. This provides for the mass functionalization of nanopipettes a MEMS wafer level manufacturing and eliminates the manual functionalization of each nanopipette and the associated surface chemistry contamination risk from manual operation.

Figure 4A:
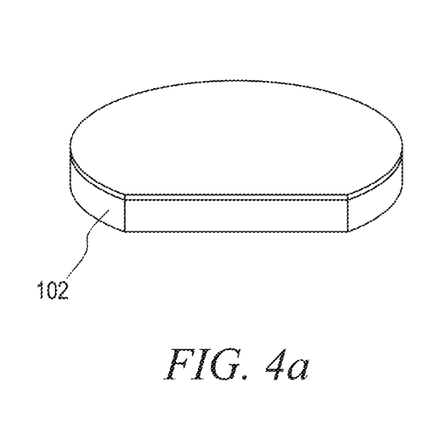
FIGS. 4a-4d illustrate forming a silicon on insulator wafer.

FIG. 4a illustrates base substrate wafer 102, such as silicon, germanium, aluminum phosphide, aluminum arsenide, gallium arsenide, gallium nitride, indium phosphide, silicon carbide, or other bulk semiconductor material. Base substrate wafer 102 has a thickness of 300-500 micrometers (μm) and is prepared by grinding and polishing.

Figure 4B:
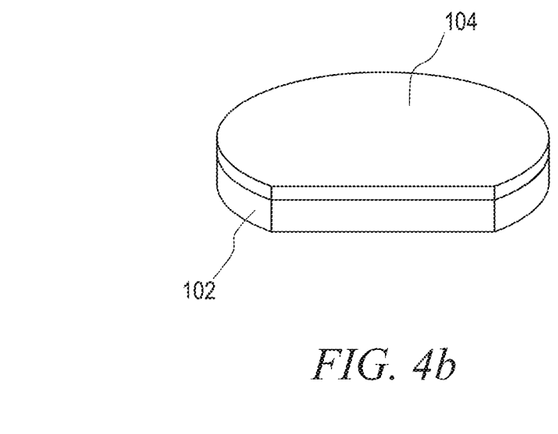
Figure 4C:
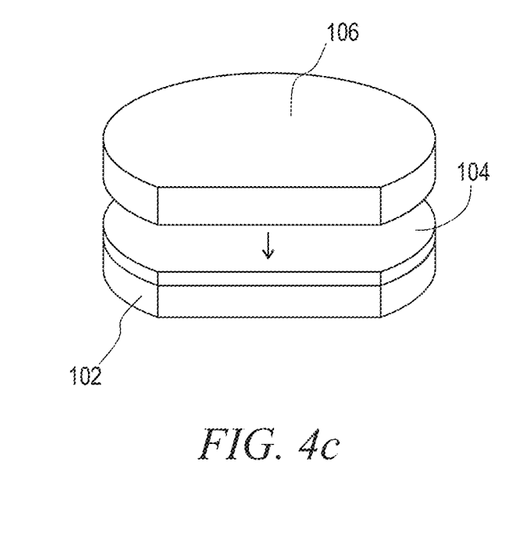
Figure 4D:
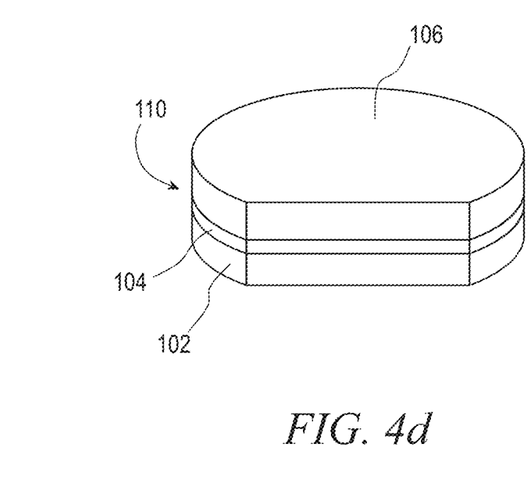

In FIG. 4b, buried oxide layer 104 is formed over base substrate wafer 102 by high temperature thermal growth. Buried oxide layer 104 contains one or more layers of silicon dioxide (SiO2), silicon nitride (Si3N4), silicon oxynitride (SiON), tantalum pentoxide (Ta2O5), aluminum oxide (Al2O3), and other material having similar insulating and structural properties. In FIG. 4c, device layer 106 is joined by high temperature fusion bonding or other direct wafer bonding (DWB). In DWB, device layer 106 is first bonded to base substrate wafer 102 at room temperature using macroscopic short-range surface forces. Next, device layer 106 and base substrate wafer 102 are heated to form strong primary bonds at the interface. The DWB process is attractive, as it allows high-strength bonds that are stable at high temperatures to be formed without the introduction of a bonding interlayer or the application of clamping loads during thermal treatment. DWB is particularly useful in the manufacture of MEMS. Device layer 106 can be silicon, germanium, aluminum phosphide, aluminum arsenide, gallium arsenide, gallium nitride, indium phosphide, silicon carbide, or other bulk semiconductor material. FIG. 4d shows SOI wafer 110 including base semiconductor wafer 102, buried oxide layer 104, and device layer 106. SOI wafer 110 undergoes device preparation including high precision grinding and polishing. In one embodiment, SOI wafer 110 has a width or diameter of 100-450 millimeters (mm) and thickness of about 0.4 to 1.0 mm.

Figure 5A:
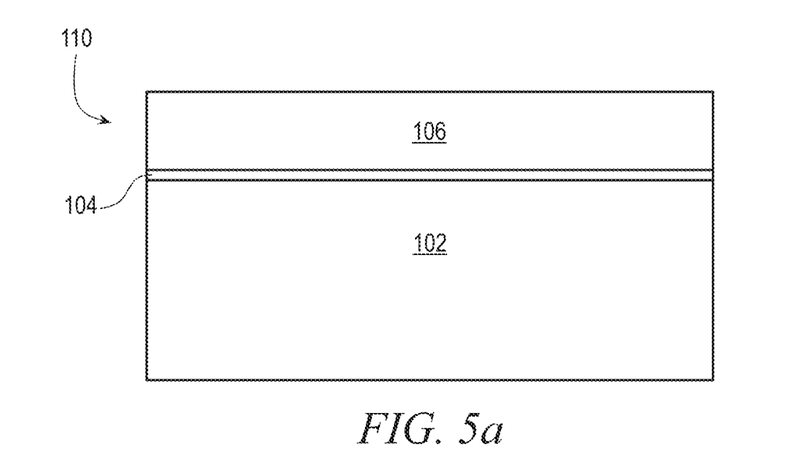
FIGS. 5a-5l illustrate a process of forming a semiconductor biosensor with an SOI MEMS structure.
Figure 5B:
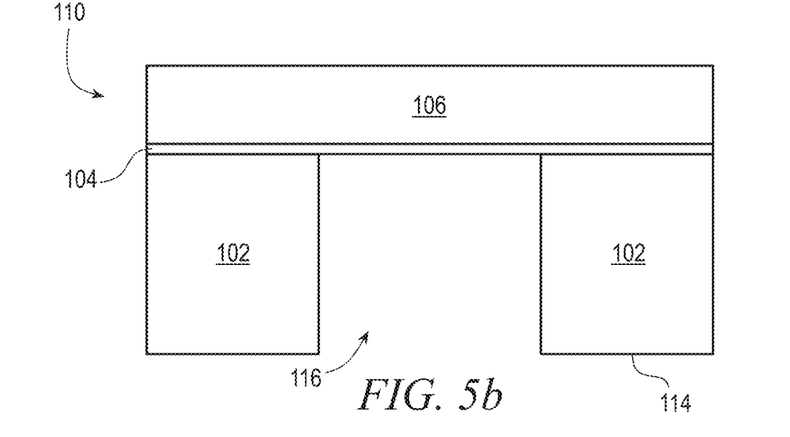

FIGS. 5a-5l illustrate formation of a biosensor using SOI MEMS, DRIE, and ALD techniques to make a semiconductor device capable of detecting a pathogen. FIG. 5a illustrates a portion of SOI wafer 110 including base semiconductor wafer 102, buried oxide layer 104, and device layer 106. In FIG. 5b, surface 114 of base semiconductor wafer 102 is cavity-SOI etched to form cavity or opening 116 extending through the base semiconductor wafer to buried oxide layer 104 using deep reactive ion etching (DRIE). The DRIE is a highly anisotropic etch process used to create deep penetration, steep-sided holes, cavities, and trenches in wafers/substrates, typically with high aspect ratios. To create deep anisotropic etching of silicon, the etch process switches between different plasma chemistries to provide fluorine-based etching of the silicon while protecting the sidewall of the growing feature with a fluorocarbon layer. A $C_4F_8$ plasma deposits a fluoropolymer passivation layer onto the mask and into the etched feature. A bias from the platen causes directional ion bombardment resulting in removal of the fluoropolymer from the base of the feature and the mask. The fluorine free radicals, in the $SF_6$ plasma, etch the exposed silicon at the base of the etch feature isotropically. The DRIE process repeats multiple times to achieve a vertical etch profile for cavity 116. A backside wet etch stopping on buried oxide layer 104 is also an advantage of SOI wafer 110. Buried oxide removal by wet or vapour HF allows the structure in FIG. 5b to be highly manufacturable.

Figure 5C:
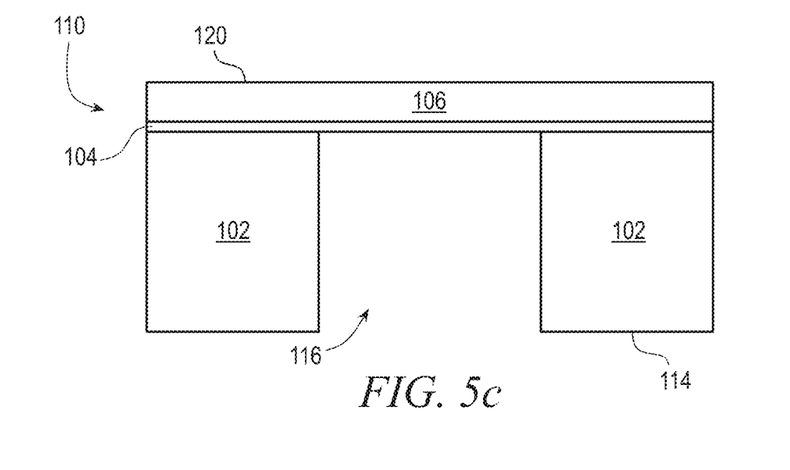

In FIG. 5c, surface 120 of device layer 106 is photoresist stripped and cleaned. The thickness of device layer 106 is reduced to about 5 μm.

Figure 5D:
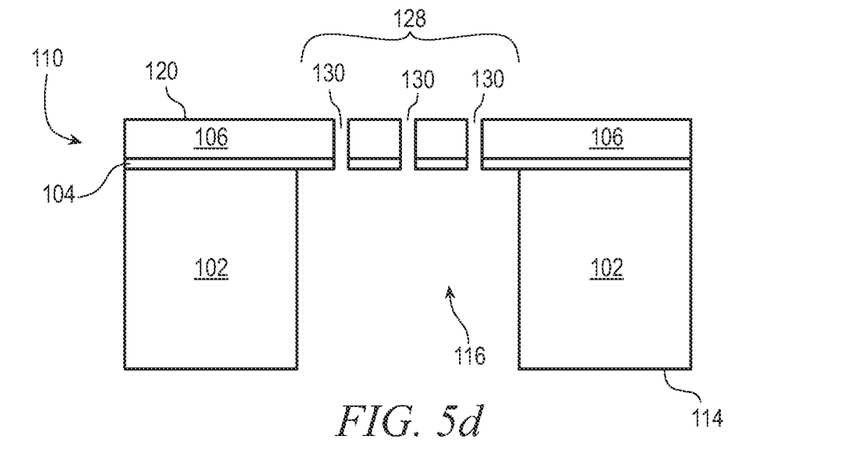

In FIG. 5d, the portion of device layer 106 spanning across cavity 116 is referred to as membrane 128. Openings 130 are formed through the membrane portion of device layer 106 using front side aperture photolithograph with 2 μm critical dimension and DRIE. Openings 130 extend to cavity 116. The processing features of DRIE can form openings 130 at 1 μm or less in diameter. SOI wafer 110 is particularly useful as buried layer 104 stops DRIE from the top and bottom surfaces of the wafer. The DRIE etch process can leave a scalloped sidewall that can cause a problem for the flow of the nasal fluid, blood, saliva, or other biofluids through the nanopipette.

Figure 5E:
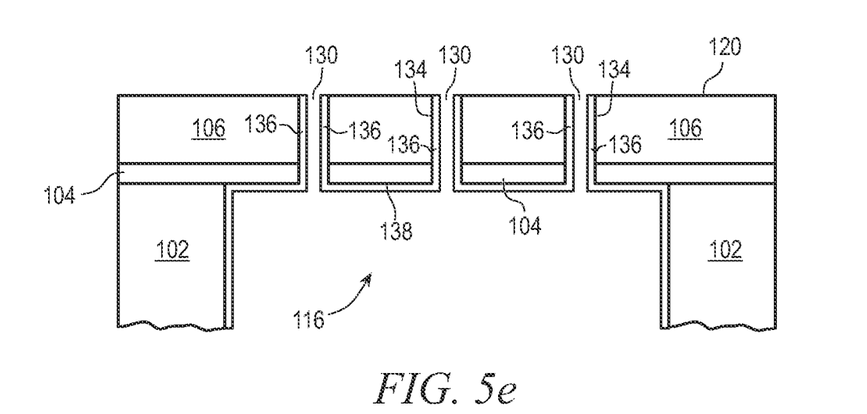
Figure 5F:
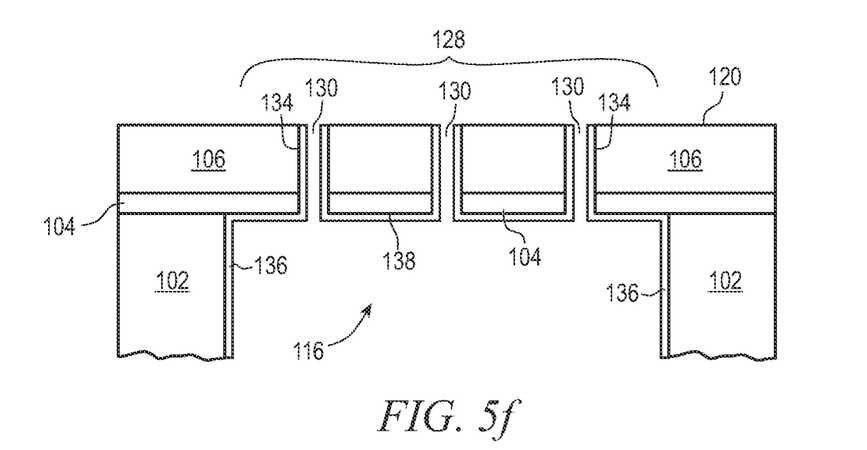
Figure 5G:
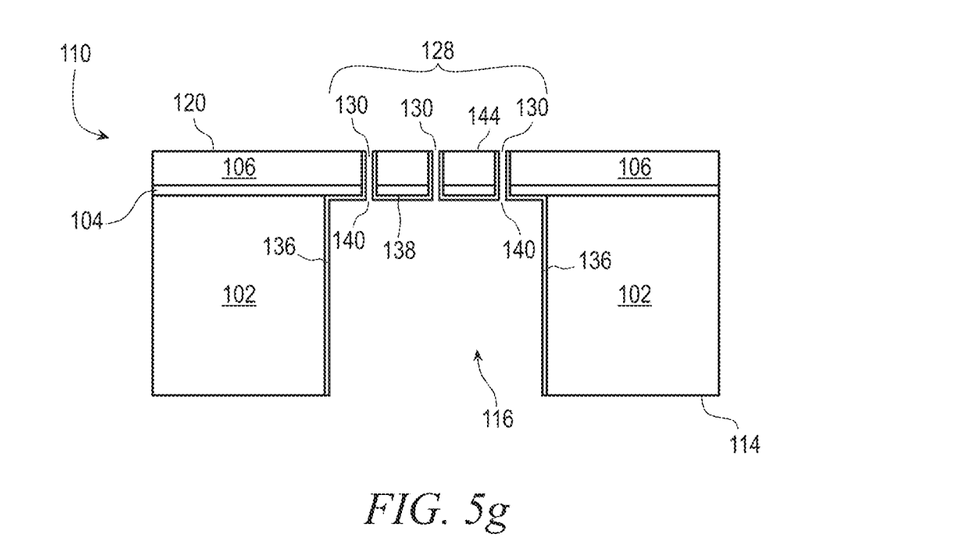

In FIG. 5e, a sacrificial thermal oxide layer 132 is grown on sidewalls 134 of openings 130. In FIG. 5f, the sacrificial thermal oxide layer 132 is removed by wet chemistry following by HF vapor phase fuming to smooth the inner wall. Another sacrificial thermal oxide layer 132 is again grown on sidewalls 134 of openings 130, as shown in FIG. 5e. The sacrificial thermal oxide layer 132 is again removed by wet chemistry following by HF vapor phase fuming to smooth the inner wall, as shown in FIG. 5f. The process of repetitive growth of thermal oxide and removal continues multiple times, in accordance with FIGS. 5e-5f, until the sidewall of opening 130 is smooth. The smooth sidewalls 134 make opening 130 hydrophilic promoting wetting to the surface, as opposed to Hydrophobic. By eliminating the scalloping from the DRIE etch and using the sacrificial thermal oxide followed by HF fuming or any oxide and silicon etches, sidewall 134 can be smoothed to a tapered form.

The smoothing process of FIGS. 5e-5f can be shown Table 1 as:

TABLE 1

| Sidewall smoothing process | |
|---|---|
| DRIE trench etch | |
| Ashing | |
| Trench etch - post clean 1 | SPM (H2SO4 + H2O2) |
| Trench etch - post clean 2 | BHF 20" |
| N column imp - pre clean | SC1 + DHF + SC2 |
| N column imp | |
| N column imp - post clean | SPM (H2SO4 + H2O2) |
| N column drive-in - pre clean | SC1 + DHF + SC2 |
| N column drive-in | Oxide thickness 640 A |
| N column wet etch | 5% HF: 10' + S/D |
| P column imp - pre clean | DHF + IPA |
| P column imp | |
| P column imp - post clean | SPM (H2SO4 + H2O2) |
| P column drive-in - pre clean | SC1 + DHF + SC2 |
| P column drive-in | Oxide thickness 630 A |
| Trench pad -OX - pre clean | SC1 + DHF + SC2 |
| Trench pad -OX | 1000 C., wet 4400 ± 400 A |

The asking step and trench etch post clean 1 step provide photoresist and contamination removal. The trench etch post clean 2 step provides for removal of O3TEOS on SiN at about 700 angstroms (A). The N column implant (imp)—pre clean step provides cleaning prior to implant. The N column imp—post clean step removes contamination after implant. The N column drive-in—pre clean step provides cleaning prior to diffusion. The N column wet etch step removes oxide film from N column drive-in. The P column imp—pre clean step cleans isopropyl alcohol (IPA) dry. The P column imp—post clean step removes contamination after implant. The P column drive-in—pre clean step provides cleaning for diffusion. Trench pad—OX—pre clean step provides cleaning for diffusion. Trench pad—OX step improves occurrence of crystal defect after tetraethyl orthosilicate (TEOS) deposition.

The removal of the inner sidewall scallops is important to the surface chemistry that enables an electrical signal to be generated that is directly proportional to the viral load. A continuous current should be able to flow through the core without high resistance presented by the sidewall of the core itself due to scallops obstructing flow of fluid. Core 140 should be tapered with the wider portion proximate to surface 120, and the narrower portion proximate to cavity 116. An opposite taper is also possible.

Figure 5H:
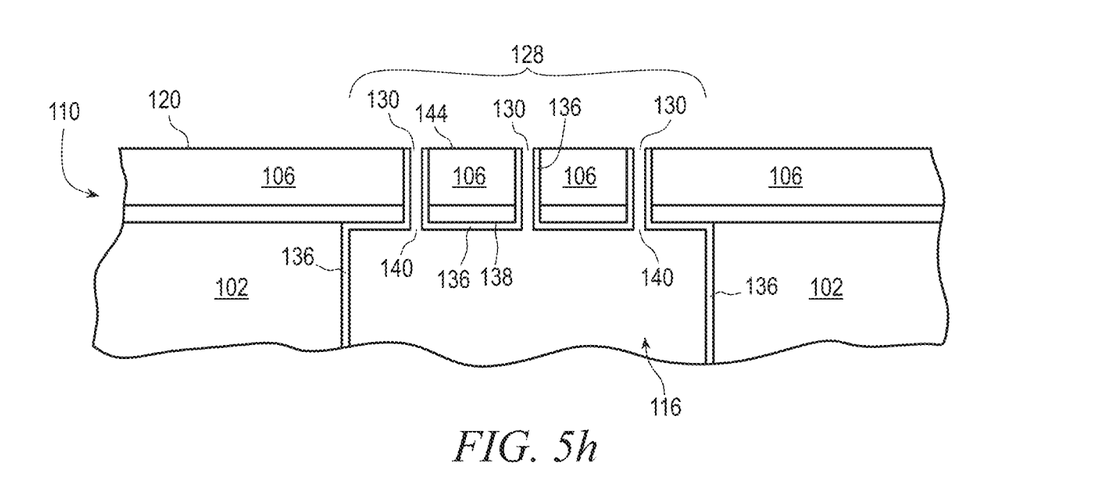

Returning to FIG. 5g, a layer of material 136 is deposited on sidewalls of cavity 116, backside surface 138 of membrane 128, and on sidewalls of openings 130 using ALD. In one embodiment, layer of material 136 is alumina or aluminum oxide ($Al_2O_3$). Alternatively, layer of material 136 can be any material that enhances wetting of the nasal fluid, blood, saliva, or other biofluids through core 140, in addition to precisely controlling the diameter of the core and thickness of the electrode on the backside of the membrane. FIG. 5h provides closer detail of membrane 128. Core 140 is defined as the pathway through membrane 128 with alumina 136 on the sidewalls of openings 130. Core 140 functions similar to nanopipette 50. A biofluid sample will be deposited on surface 144 of membrane 128. A portion of the biofluid sample travels through core 140 to cavity 116 which will contain the antibody reagent solution. The ALD process allows the diameter of core 140 to be highly controlled ranging from 50 nm to 2.0 which in turn controls the amount of biofluid sample passing through the core to cavity 116. The ratio of the span of membrane 128 to the thickness of the membrane is about 5:1 to provide robustness for the pathogen testing process. The thickness of membrane 128 ranges from 2-20 μm. In one embodiment, the span of membrane 128 is 25 μm and the thickness of the membrane is 5 μm. The shape and dimensions of core 140 are important to the accuracy and performance of the biosensor. The combination of DRIE in forming openings 130 and ALD of alumina to precisely set the diameter of core 140 provides a controllable and repeatable SOI MEMS manufacturing process.

The core thickness is related to the current flow and desired to be less than 400±20 nanometers (nm). ALD provides a close tolerance on core thickness by depositing an electrical insulator on sidewall of the core to control thickness and provide electrical isolation, hydrophilic property, and conformal coating.

Figure 5I:
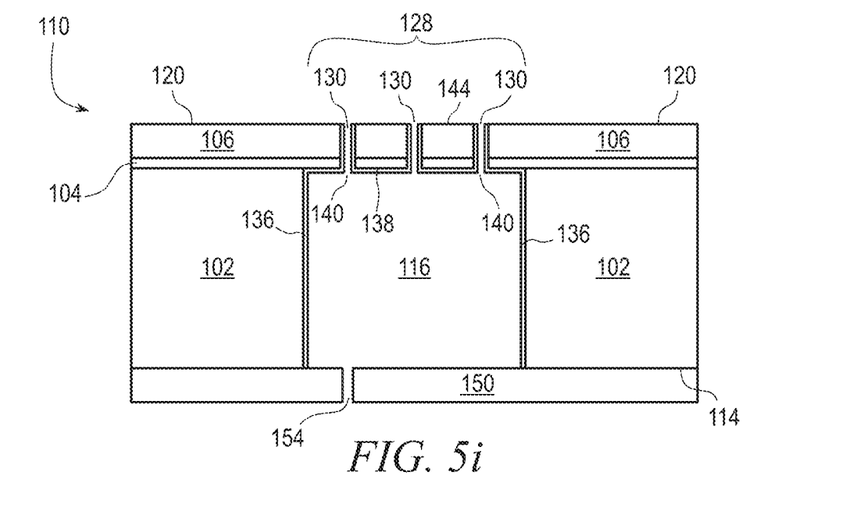

In FIG. 5i, CSOI backside contact 150 is formed over surface 114 of base substrate 102 using DWB. In another embodiment, CSOI backside contact 150 is performed after cavity 116 is formed in base substrate wafer 102. SOI 110 and membrane 128 are formed after CSOI backside contact 150 is formed. CSOI backside contact 150 includes port 154 to fill cavity 116 with antibody reagent solution post manufacturing.

Figure 5J:
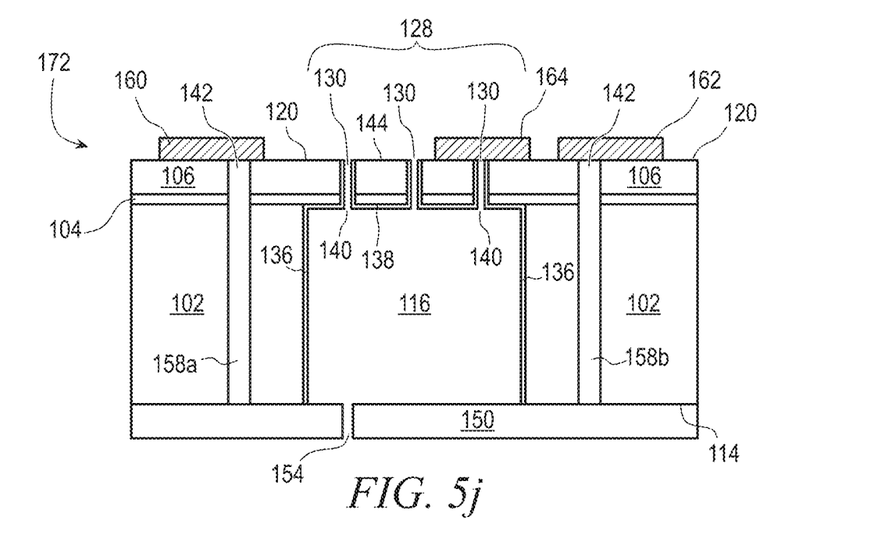

In FIG. 5j, vias are formed from surface 120 through device layer 106 and base substrate wafer 102 to CSOI backside contact 150. The vias are filled with doped polysilicon or other conductive material to form through conductive silicon vias (TSV) 158a and 158b. Alternatively, TSVs 158a-158b can be metal pillars, such as Cu. Electrically conductive layers 160, 162, and 164 are formed over surface 120 using PVD, CVD, electrolytic plating, electroless plating process, or other suitable metal deposition process. Conductive layers 160, 162, and 164 can be one or more layers of aluminum (Al), copper (Cu), tin (Sn), nickel (Ni), gold (Au), silver (Ag), or other suitable electrically conductive material. Conductive layer 160 makes electrical connection to TSV 158a. Conductive layer 162 makes electrical connection to TSV 158b. Conductive layer 164 makes electrical connection through device layer 106 to the antibody reagent solution in cavity 116. Accordingly, TSV 158 provide electrical connection between the front side and backside of biosensor 172.

Figure 5K:
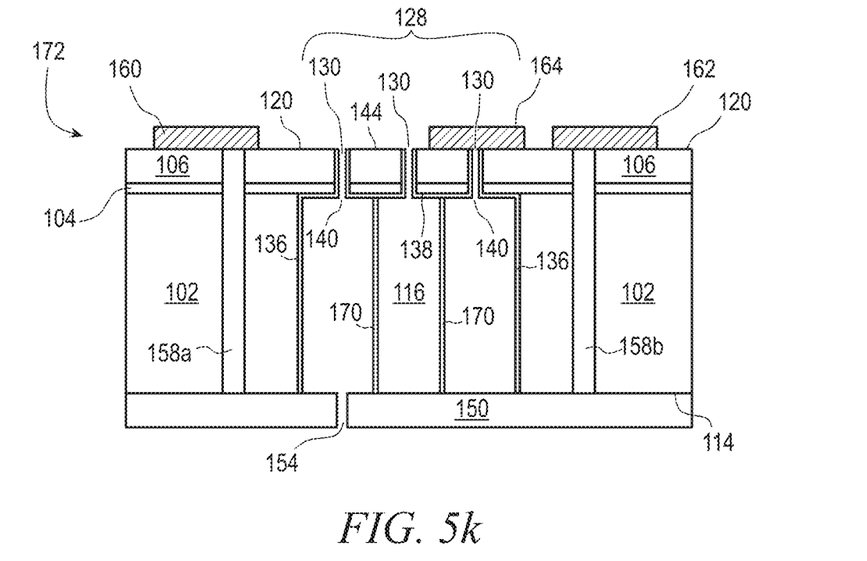

Membrane 128, which is the span of device layer 106 above reagent cavity 116, is formed using direct wafer bonding silicon on oxide (SOI) and serves as a structural member to make the device more robust. The membrane alumina-lined SOI can also have silicon hexagonal posts created by photolithogrpahy and DRIE etch that further supports the membrane at various locations across the cavity at a low density not to impact the microfluidic flows of reagent solution when converted from vapor phase to liquid solution. FIG. 5k shows an embodiment with silicon posts or pillars 170 disposed in cavity 116 to provide additional support for membrane 128.

Figure 5L:
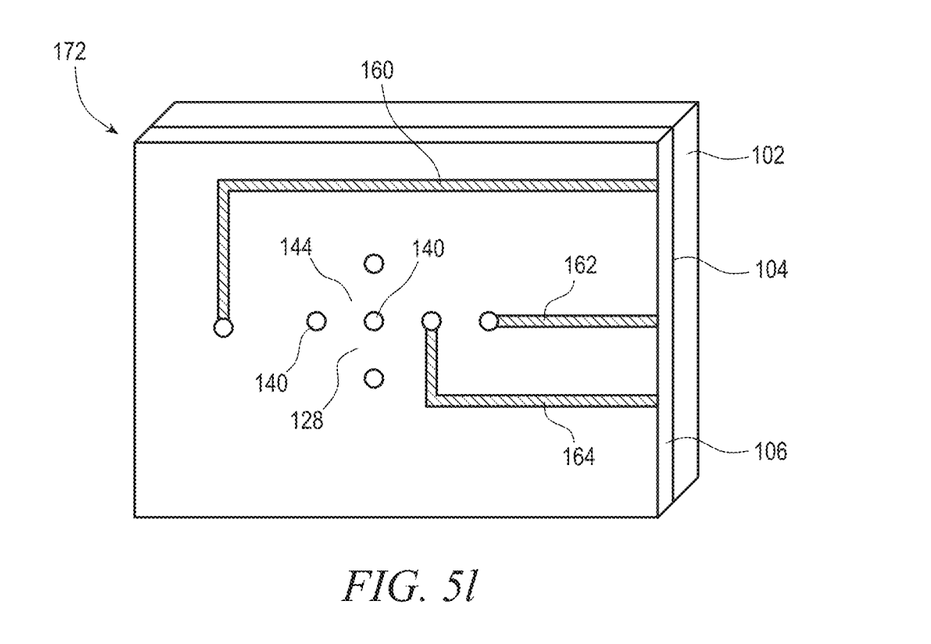

FIG. 5l is a top view of biosensor 172 with membrane 128, cores 140, and conductive layers 160-164.

Biosensor 172 can be used to test for a variety of pathogens. In one embodiment, the pathogen to be tested is the SARS-COV-2 virus. Biosensor 172 is based in part on SOI MEMS technology, and in particular uses DRIE to create openings and ALD to form alumina within those openings. DRIE and ALD provides precise control and repeatable manufacturability over the shape and size of core 140 in membrane 128, which are key to accurate and efficient testing.

Biosensor 172 is typically sent post manufacturing to a lab or medical facility to inject the desired antibody reagent solution through port 154 and into cavity 116. The antibody reagent solution is selected according to the pathogen to be detected. For example, the antibody reagent solution may be selected that reacts with the specific SARS-COV-2 particle. Biosensor 172 can be configured to detect other pathogens by selection of the corresponding antibody reagent solution. However, the medical facility injecting the desired antibody reagent solution manually into every biosensor port 154 and cavity is a very slow process to functionalize the biosensor. The use of a sacrificial thermal oxide grown on the inner wall of the nanopipette and then removed by wet chemistry followed by HF vapor phase fuming to smooth inner wall provides the microfluidic control of the target sample enabling sensitivity and accuracy. The application of ALD to control the diameter of the nanocore plus the use of atomic level vapor phase deposition of the reagent buffer solution to mass functionalize each nanopipette in wafer form makes this a novel high volume mass production worthy technology.

Figure 6:
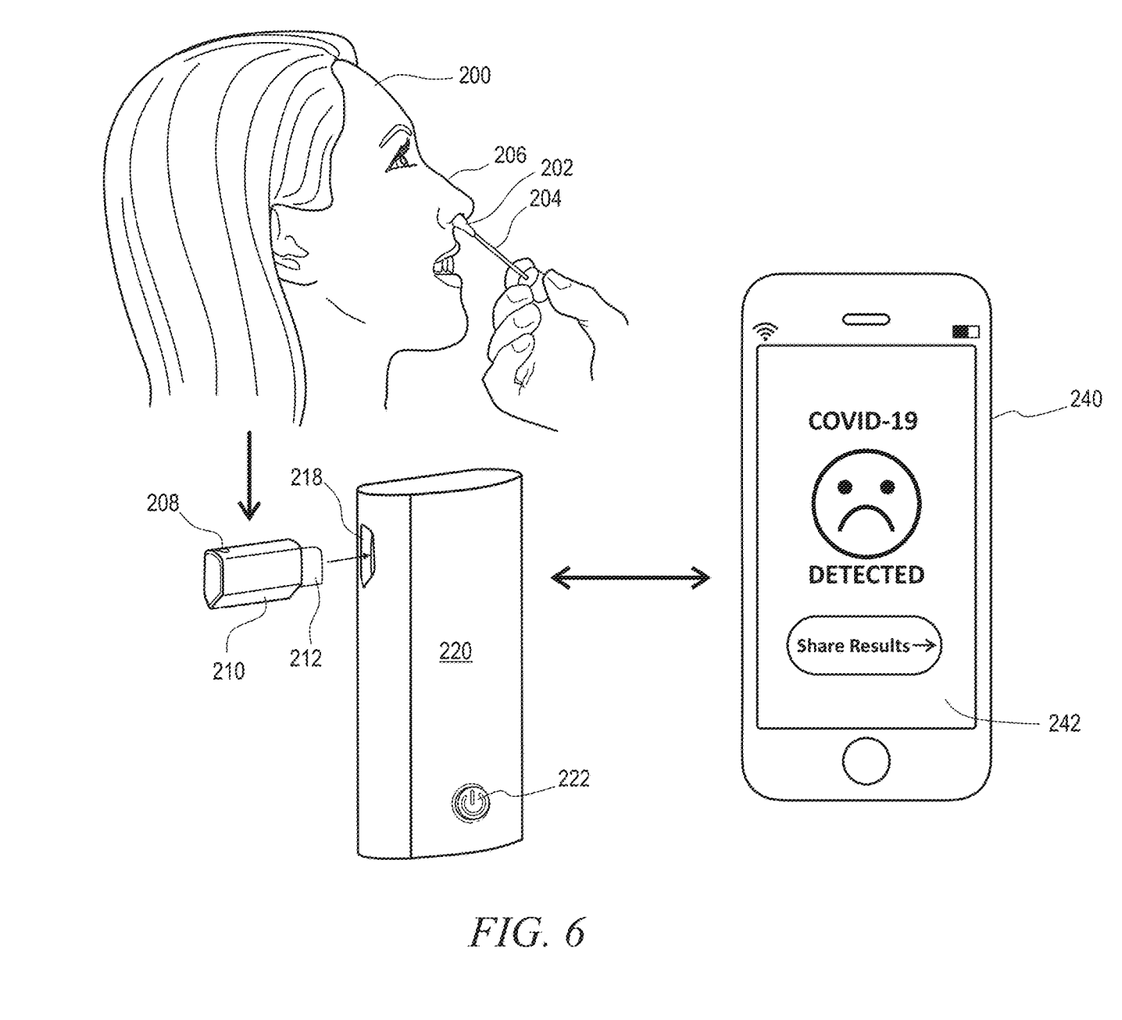
FIG. 6 illustrates the biosensor test for a pathogen.
Figure 7:
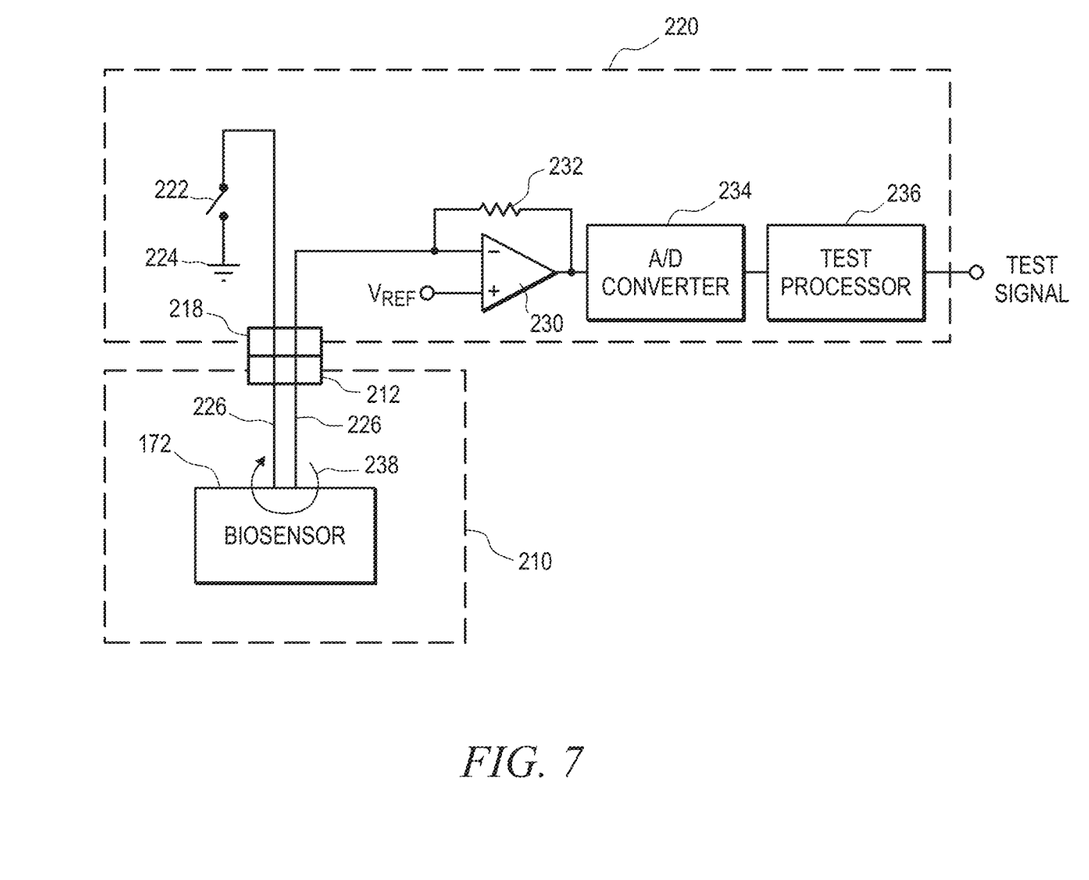
FIG. 7 illustrates a current detection circuit to test for the pathogen.

Biosensor 172, loaded with the antibody reagent solution that reacts with the SARS-COV-2, can be sent to the field for testing purposes. FIG. 6 illustrates testing on human subject 200 using biosensor 172. Nasopharyngeal test swab 204 is taken from nasal cavity 206 of human subject 200. Test swab 204 contains biofluid 202. Test swab 204 with biofluid 202 is inserted into opening 208 of test unit 210. Test unit 210 is a one-time use, disposable cartridge. Test unit 210 contains biosensor 172 and includes electrical connector 212, which is connected to conductive layers 160, 162, and 164 on biosensor 172. Electrical connector 212 is inserted into electrical receptacle 218 of tester 220. Placing test swab 204 in opening 208 causes biofluid 202 to be deposited on surface 144 of membrane 128. Accordingly, a sufficient amount of biofluid 202 to perform the test is deposited on surface 144 of membrane 128. Biofluid 202 can be nasal fluid, saliva, blood, and other bodily fluids. Biofluid 202 is drawn through core 140 and introduced into cavity 116 to mix with the antibody reagent solution. Alumina 136, as deposited by ALD on inner walls of hole 130 and on surface 138 inside cavity 116, controls the width of core 140 to pass a known amount of biofluid 202 to react with the antibody reagent solution. If present, SARS-COV-2 virus particles bond with the antibody reagent solution specifically selected for such reaction, i.e., SARS-COV-2 test. Alumina 136 acts as an electrode host that is in intimate contact with the antibody reagent solution. These antibodies are attracted to the alumina electrode host in core 140 and on surface 138 of membrane 128. An ionic current is generated as SARS-COV-2 virus particles interact with the antibody reagent solution along the alumina electrode host in core 140 and on surface 138 of membrane 128. The SARS-COV-2 virus particles chemically reacting with the antibody reagent solution, i.e., antibodies combining with SARS-COV-2, changes the impedance in the ionic current path. The antibody-antigen reaction in the sample solution causes a change in the surface charge as a result changing the conductivity of the solution. That change in conductivity measures the concentration of the target SARS-COV-2 and provides a measurement proportional to the viral load of the nanoparticles infecting the human cells.

Test unit 210 is one-time use and disposable having been contaminated with biofluid 202 from human subject 200. Tester 220 is reusable and contains electrical circuitry necessary to measure an ionic current. FIG. 7 illustrates components of test unit 210 and tester 220. In tester 220, test button 222 closes current path 226 to ground terminal 224. Current path 226 through biosensor 172 passes through conductive layer 164, core 140, antibody reagent solution, CSOI backside contact 150, TSVs 158*a*-158*b*, conductive layers 160 and 162 of biosensor 172. Current path 226 continues through connector 212 and receptacle 218 to the inverting input of low noise amplifier 230. The non-inverting input of amplifier 230 receives a reference voltage $V_{REF}$. Resistor 232 is connected between the output of amplifier 230 and its inverting input to set the gain of the amplifier. The output of amplifier 230 is routed through analog-to-digital converter 234 to test processor 236 to analyze the measurements, see FIG. 6. Test processor 236 transmits the test signal to test receiver 240 by wireless transmission, e.g., Bluetooth or WiFi, or by direct electrical connection. In one embodiment, test receiver 240 is a smart phone with display 242 to show test results.

Upon depositing the biofluid into opening 208 of test unit 210, inserting connector 212 into receptacle 218, and pressing activate test button 222, tester 220 completes current path 226 and allows current to flow in the direction of arrow 238. If the biofluid contains no SARS-COV-2, the impedance in current path 226 remains at its nominal value and the ionic current flowing through current path 226 remains at its nominal value. If the biofluid contains SARS-COV-2, the antibodies combine with the SARS-COV-2 particles changing the impedance of solution in proximity of the alumina 136 electrode. The change in impedance of the alumina electrode causes a change in the ionic current accompanying the chemical reaction that takes place when the antibodies combine with the SARS-COV-2 particles. The impedance in current path 226, particularly through the alumina 136 electrode on surface 138 and in core 140, increases from its nominal value and the ionic current flowing through current path 226 decreases from its nominal value. The decrease in the ionic current is proportional to the amount or concentration of the SARS-COV-2 particles in the test. Accordingly, biosensor detect the presence and concentration of the SARS-COV-2. Test unit 210 with biosensor 172 simplifies and reduces the antibody-antigen reaction test to less than 30 seconds, making the test practical for mass testing at mass screening, such as schools, workplaces, universities, and entertainment and sports venues. Again, other pathogens can be detected by matching with the appropriate reactant antibody solution.

In summary, infectious diseases have been a leading cause of mortality worldwide, with viruses making global impact on healthcare and socioeconomic development. The rapid development of drug resistance to currently available therapies and adverse side effects due to prolonged use is a serious public health concern. The interaction of nanostructures with microorganisms is revolutionizing the biomedical field by offering advantages in both diagnostic and therapeutic applications and the necessary diagnostic testing of these illnesses. Test unit 210 with biosensor 172 is highly manufacturable, reliable, and offers a rapid, low cost test capability. Test unit 210 in combination with tester 220 provide a handheld diagnostic unit that is easy to use, through a portable reader and disposable cartridges, with no lab, amplification, or sample prep needed. Mass screening reduces the spread of viruses, particularly during a pandemic.

Semiconductor technology, such as DRIE, DWB, and ALD, can contribute to transforming the way infectious diseases are detected, diagnosed, and surveilled by enabling a new era of biosensor point-of-care diagnostics sensors. SOI MEMS can be applied to nanopore biosensors for detection of human infectious disease diagnostics, pathogen surveillance by applying SOI MEMS to detect specific pathogens in samples of nasal fluid, blood, saliva, or other biofluids.

While one or more embodiments of the present invention have been illustrated in detail, the skilled artisan will appreciate that modifications and adaptations to those embodiments may be made without departing from the scope of the present invention as set forth in the following claims.

What is claimed:

1. A method of making a semiconductor device, comprising:

providing a substrate;

forming a buried oxide layer over the substrate;

forming a device layer over the buried oxide layer forming a cavity through the substrate while leaving the buried oxide layer disposed over the cavity, wherein a portion of the device layer and buried oxide layer disposed over the cavity forms a membrane;

forming a plurality of openings through the membrane and extending to the cavity;

depositing aluminum oxide over a sidewall of the openings through the membrane and further over the buried oxide layer within the cavity; and forming a backside contact over a surface of the substrate opposite the device layer, wherein the backside contact includes a port extending into the cavity adapted to introduce a reactive solution into the cavity.

2. The method of claim 1, further including forming the device layer over the substrate by direct wafer bonding.

3. The method of claim 1, further including forming a plurality of posts within the cavity to support the membrane at locations within the cavity.

4. The method of claim 3, further including forming the posts by deep reactive ion etching.

5. The method of claim 3, wherein the posts allow for microfluids flows of reagent solution when converted from vapor phase to liquid solution.

6. The method of claim 1, further including forming an oxide layer between the substrate and device layer.

7. The method of claim 1, further including forming a sacrificial thermal oxide on a surface within the holes.

8. The method of claim 7, further including removing the sacrificial thermal oxide.

9. The method of claim 7, further including removing the sacrificial thermal oxide by wet chemistry followed by hydrofluoric acid vapor phase fuming to smooth the surface within the holes.

10. The method of claim 1, further including depositing the aluminum oxide over a sidewall of the cavity and a surface of the buried oxide layer.

11. The method of claim 1, further including forming a backside contact over a surface of the substrate opposite the device layer, wherein the backside contact includes a port extending into the cavity adapted to introduce a reactive solution into the cavity.

12. A method of making a biosensor, comprising:
providing a first substrate;
forming a buried oxide layer over the first substrate;
disposing a second substrate over the buried oxide layer;
forming a cavity through the first substrate while leaving the buried oxide layer disposed over the cavity, wherein a portion of the second substrate and buried oxide layer disposed over the cavity forms a membrane;
forming a plurality of holes through the membrane including the second substrate and the buried oxide layer disposed over the cavity; and
forming a backside contact over a surface of the substrate opposite the device layer, wherein the backside contact includes a port extending into the cavity adapted to introduce a reactive solution into the cavity.

13. The method of claim 12, further including forming the holes through the second substrate by atomic level deposition.

14. The method of claim 12, further including forming a sacrificial thermal oxide on a surface within the holes.

15. The method of claim 14, further including removing the sacrificial thermal oxide by wet chemistry followed by hydrofluoric acid vapor phase fuming to smooth the surface within the holes.

16. The method of claim 14, further including removing the sacrificial thermal oxide by wet chemistry followed by hydrofluoric acid vapor phase fuming to smooth the surface within the holes.

17. The method of claim 12, further including forming a layer of material over a surface of the cavity and into the holes to form a plurality of cores.

18. The method of claim 12, further including introducing a reagent solution in vapor phase through the port and into the cavity.

19. The method of claim 18, further including introducing the reagent solution in vapor phase into the cavity by atomic level vapor phase deposition.

20. The method of claim 18, wherein introducing the reagent solution in vapor phase into the cavity by atomic level vapor phase deposition provides mass functionality of the cores.

21. The method of claim 12, further including depositing aluminum oxide over a sidewall of the openings through the membrane and further over the buried oxide layer within the cavity.

22. A method of making a biosensor, comprising:
providing a substrate;
forming a buried oxide layer over the substrate;
disposing a device layer over the buried oxide layer;
forming a cavity through the substrate while leaving the buried oxide layer disposed over the cavity to form a membrane as a portion of the device layer and buried oxide layer disposed over the cavity; and
forming a plurality of holes through the membrane including the device layer and the buried oxide layer disposed over the cavity.

23. The method of claim 22, further including forming a sacrificial thermal oxide on a surface within the holes.

24. The method of claim 23, further including removing the sacrificial thermal oxide.

25. The method of claim 22, further including forming a layer of material over a surface of the cavity and into the holes to form a plurality of cores.

26. The method of claim 22, further including forming the holes through the device layer by atomic level deposition.

27. The method of claim 22, further including introducing a reagent solution in vapor phase through the port and into the cavity.

28. The method of claim 27, further including introducing the reagent solution in vapor phase into the cavity by atomic level vapor phase deposition.

* * * * *